United States Patent [19]
Angel et al.

[11] Patent Number: 6,140,335
[45] Date of Patent: Oct. 31, 2000

[54] USE OF MIZOLASTINE FOR TREATING INFLAMMATORY DISEASES ASSOCIATED WITH 5-LIPOXYGENASE

[75] Inventors: Itzchak Angel, Nes-Ziona, Israel; Sonia Arbilla, Paris, France; Luc Even, Paris, France; Jonathon Marc Goldhill, Paris, France; Philippe Pichat, Orsay, France; Nigel Oliver Roome, Versailles, France

[73] Assignee: Sanofi-Synthelabo, Paris, France

[21] Appl. No.: 09/403,005

[22] PCT Filed: Apr. 16, 1998

[86] PCT No.: PCT/FR98/00765
§ 371 Date: Nov. 19, 1999
§ 102(e) Date: Nov. 19, 1999

[87] PCT Pub. No.: WO98/47511
PCT Pub. Date: Oct. 29, 1998

[30] Foreign Application Priority Data

Apr. 17, 1997 [FR] France .................................. 97 04801

[51] Int. Cl.⁷ .................................................. A61K 31/505
[52] U.S. Cl. .............................................................. 514/272
[58] Field of Search ............................................. 514/272

[56] References Cited

U.S. PATENT DOCUMENTS 4,912,219  3/1990  Manoury et al. ........................ 544/321

OTHER PUBLICATIONS

Levrier, J. et al. "Anti–anaphylactic Activity of the Novel Selective Histamine H1 Receptor Antagonist Mizolastine in the Rodent", Drug Res., vol. 45, No. 5, 1995, pp. 559–568.

Leynadier, F. et al, "Efficacy and safety of mizolastine in seasonal allergic rhinitis", Annals of Allergy, Asthma and Immunology, vol. 76, No. 2, 1996, pp. 163–168.

Pinquier, J–L. et al, "Effect of mizolastine on experimental inflammation in human shin", Clinical Pharmacology and Therapeutics, vol. 57, No. 2, 1995, p. 169.

Angel, P. et al, "Powerful antihistamine properties of mizolastine in cutaneous oedema in the dog", Allergy, vol. 51, No. 31, 1996, p. 171.

*Primary Examiner*—William R. A. Jarvis
*Attorney, Agent, or Firm*—Jacobson, Price, Holman & Stern, PLLC

[57] ABSTRACT

The invention concerns the use of mizolastine and the pharmaceutically acceptable salts thereof for making a medicine for treating inflammatory diseases or inflammatory constituents of some other diseases related to the 5-lipoxygenase route.

9 Claims, No Drawings ical and US OF MIZOLASTINE FOR TREATING
INFLAMMATORY DISEASES ASSOCIATED
WITH 5-LIPOXYGENASE This application is a 371 of PCT/FR98/00765, filed Apr. 16, 1998.

The present invention relates to the use of mizolastine, 2-[[1-[1-[(4-fluorophenyl)methyl]-1H-benzimidazol-2-yl]-4-piperidyl]methylamino]-4-pyrimidinol or 2-[[1-[1-[(4-fluorophenyl)methyl]-1H-benzimidazol-2-yl]-4-piperidyl]methylamino]pyrimidin-4(1H)-one, and pharmaceutically acceptable salts thereof, for the preparation of a medicament intended for treating inflammatory diseases or inflammatory components of certain other diseases, associated with the 5-lipoxygenase route.

Mizolastine and pharmaceutically acceptable salts thereof are described in European Patent EP 0,217,700. Mizolastine is known as a histamine (H1) receptor antagonist and is used in the treatment of various allergic manifestations.

Certain documents which discuss mizolastine mention its effect in allergic inflammations associated with the release of histamine: Levrier et al., "Anti-anaphylactic activity of the novel selective histamine H1 receptor antagonist mizolastine in the rodent", Arzneimittelforschung, 45(5), 559–568 (1995); Leynadier et al., "Efficacy and safety of mizolastine in seasonal allergic rhinitis", Annals of Allergy, asthma and immunology, 76(2), 163–168 (1996); Pinquier et al., "Effect of mizolastine on experimental inflammation in human skin", Clinical pharmacology and therapeutics, 57(2), 169 (1995); Angel et al., "Powerful antihistamine properties of mizolastine in cutaneous oedema in the dog", Allergy, 51(31), 171 (1996).

In the cases described in these documents, these are inflammatory reactions induced indirectly by histamine (His), as described by R. Anderson et al. in "The in vitro effects of histamine and metiamide on neutrophil motility and their relationship to intracellular cyclic nucleotide levels", J. Immunol., 118, 1690–1697 (1977).

In effect, histamine (His) is not, strictly speaking, an inflammation mediator, but is involved in the physiological alteration during the established inflammatory processes. His is mainly released in response to stimulation with an antigen, to certain cellular inflammation factors or to physical stimuli. The direct role of His has been described and characterized in the allergic reactions, but only in acute phases of the allergy. His is not considered as being directly involved in initiating inflammation in delayed phases of the allergy (Tannenbaum et al. J. Immunol. 125, 325).

His is an amine which is essentially stored in the mastocyte and basophil cells. It is single-handedly capable of producing intradermal effects of vasodilation and of increasing local vascular permeability or of pain, i.e. only 3 of the 5 cardinal signs of inflammation. Thus, as regards the main inflammatory cells, i.e. the neutrophils (myeloid cells), histamine does not by itself modify the basal chemotaxis of these cells. Furthermore, His affects only the already-stimulated cellular chemotaxis which is associated with the intracellular increase in the level of cyclic adenosine 3',5'-monophosphate (cAMP), mainly by means of the agonist activity of the histamine $H_2$-receptor subtypes.

In contrast with His, leukotrienes play a key role in inflammatory responses and are involved in generating many different inflammatory pathologies.

More precisely, leukotrienes are in fact derived from a common precursor, leukotriene A4 (LTA4). The latter is formed only after an intermediate step in which hydroxyperoxyeicosatrienoic acid (5-HPETE) is synthesized by the action of 5-lipoxygenase (5-LO) on arachidonic acid (AA).

Thus, reduction of the 5-LO route is one possible way of inhibiting the production of the leukotrienes involved in the inflammatory processes (Bell et al., Journal of Lipid Meditors, 6, 259–264, 1993; R. M. McMillan and E. R. H. Wlaker, Trends Pharmacol. Sci., 13, 323–330, 1992).

It should also be pointed out that, further upstream, the primary sites of activation of arachidonic acid biosynthesis following an inflammatory stimulus are limited to the myeloid cells (neutrophils, eosinophils, etc.), (leading to 5-LO metabolites) and are dependent on a mechanism of calcium translocation from the cytosol to the cell membrane. This mechanism for transducing the inflammatory message is consequently entirely different from the one known for His, which itself is linked to the nucleotide transduction system (cyclic AMP/cyclic GMP).

The Applicant has found that mizolastine inhibits 5-LO. The subject of the present invention is thus the use of mizolastine and pharmaceutically acceptable salts thereof for the preparation of a medicament intended for treating inflammatory diseases or inflammatory components of certain other diseases, which are linked to the 5-LO route.

Mizolastine was tested "in vitro" on 5-LO and "in vivo" in inflammation models in rats.

The "in vitro" activity of mizolastine was studied on 5-LO in rats and in man.

EXAMPLE 1

Inhibition of 5-LO in Rats

The tests were carried out according to the procedure described by R. W. Egan and P. H. Gale in J. Biol. Chem., 260, 1154–1159, 1985, with 5-LO obtained from a preparation of rat leukaemic basophil cells (RBL-1). Mizolastine is incubated with the enzyme for 5 minutes at room temperature and the reaction is initiated by addition of linoleic acid. After incubating for 8 minutes at room temperature, the reaction is stopped by addition of sodium hydroxide and the absorption is read at 234 nm in order to determine the level of 5-HETE.

The mizolastine activity, expressed as an inhibitory concentration ($IC_{50}$), is 4.6 µM.

EXAMPLE 2

Inhibition of 5-LO in Man

Mizolastine was tested on 5-LO isolated from commercial HL60 cells. The mizolastine is incubated for 10 minutes at room temperature in the presence of arachidonic acid (0.4 µM) and 5-LO. The experiment is carried out simultaneously in the presence of nordihydrogualaretic acid as reference product. The amount of 5-HETE formed is determined by RIA (Coffrey et al., J. Biol. Chem., 267–270, 1992).

The mizolastine activity, expressed as an inhibitory concentration ($IC_{50}$), is 16 µM.

The in vivo activity of mizolastine was studied in a model of inflammation of rat limbs and in a model of inflammation of rat colitis.

EXAMPLE 3

In Vivo Activity of Mizolastine in a Model of Inflammation of Rat Limbs a) inflammation by injection of AA Inflammatory oedema of rat limbs induced by the injection of AA is produced and evaluated according to the method of Di Martino et al. (*Agents and actions*, 21, 303–305, 1987) except that the AA concentration used is 0.3% (v/v).

The mizolastine is given orally 2 hours before the injection of AA. An AA solution, prepared at the time of use in a buffer solution (0.1 ml; 0.2 M carbonate; pH=11.2), is injected into the subplantar part of a rat's right hind limb.

The volume of the inflammatory reaction is measured by plethysmography after 1, 2, 3 and 4 hours.

Mizolastine at a dose of 0.3 mg/kg imparts a long-lasting inhibition of 55%, relative to the control, of the inflammation induced after 4 hours.

EXAMPLE 4

In Vivo Activity of Mizolastine in a Model of Inflammation of Experimental Colitis in Rats Mizolastine was studied in a model of rat rectocolitis induced by trinitrobenzenesulphonic acid (TNBS), according to the method described by Morris et al. (*Gastroenterology*, 96, 795–803, 1989).

The mizolastine is given orally (3 mg/kg) one hour before and one day after the instillation of TNBS (40 mg/kg in 50% ethanol) into the distal part of the colon. After 3 days, measurement of the macroscopic index of the damage, of the oedema/hypertrophy (weight of tissues) and of the myeloperoxidase activity, as a measure of the infiltration of the neutrophils, is carried out. Mizolastine imparts a significant reduction in the damage, in the oedema/hypertrophy (weight of tissues) and in the myeloperoxidase activity of 67%, 57% and 66% respectively at 3 mg/kg.

The results of these tests show that mizolastine and pharmaceutically acceptable salts thereof can be used for the manufacture of medicaments intended for treating inflammatory diseases or inflammatory components of certain other diseases, associated with the 5-LO route, among which mention may be made of: allergic reactions, rhinitis, asthma, acute respiratory distress in adults, rheumatoid arthritis, cystic fibrosis, psoriasis, inflammatory intestine syndrome, gastritis, Crohn's disease, ileocolitis, enterocolitis, haemorrhagic rectocolitis (ulcerous colitis) and inflammatory colitis.

To this end, mizolastine and salts thereof can be provided in any pharmaceutical form which is suitable for oral or topical administration, in combination with suitable excipients, to allow a daily administration of from 10 to 210 mg of active principle.

What is claimed is:

1. A method for treating inflammatory diseases or inflammatory components of diseases associated with the 5-lipoxygenase route, comprising administering to a patient in need thereof an effective amount of mizolastine or a pharmaceutically acceptable salt thereof.

2. The method of claim 1, wherein the mizolastine or pharmaceutically acceptable salt thereof is administered orally.

3. The method of claim 1, wherein the mizolastine or pharmaceutically acceptable salt thereof is administered topically.

4. The method of claim 1, wherein the mizolastine or pharmaceutically acceptable salt thereof is administered in combination with an excipient.

5. The method of claim 1, wherein the mizolastine or pharmaceutically acceptable salt thereof is administered daily in a dose of 10 to 210 mg.

6. A method for inhibiting 5-lipoxygenase, comprising administering to a patient in need thereof an effective amount of mizolastine or a pharmaceutically acceptable salt thereof.

7. The method of claim 6, wherein the patient has an inflammatory disease.

8. The method of claim 7, wherein the inflammatory disease is rheumatoid arthritis, cystic fibrosis, psoriasis, inflammatory intestine syndrome, gastritis, Crohn's disease, ileocolitis, enterocolitis, hemorrhagic rectocolitis or inflammatory colitis.

9. The method of claim 6, wherein the patient has an inflammatory component of an allergic disease wherein the allergic disease is rhinitis, asthma, or acute respiratory distress in adults.

* * * * *